(12) United States Patent
Peterson

(10) Patent No.: US 7,879,031 B2
(45) Date of Patent: Feb. 1, 2011

(54) COOLED RF ABLATION NEEDLE

(75) Inventor: Darion Peterson, Boulder, CO (US)

(73) Assignee: Covidien AG, Neuhausen am Rheinfall (CH)

(*) Notice: Subject to any disclaimer, the term of this patent is extended or adjusted under 35 U.S.C. 154(b) by 551 days.

(21) Appl. No.: 11/236,400

(22) Filed: Sep. 27, 2005

(65) Prior Publication Data
US 2007/0073285 A1 Mar. 29, 2007

(51) Int. Cl.
A61B 18/14 (2006.01)
(52) U.S. Cl. .......................................................... 606/41
(58) Field of Classification Search .................. 606/25, 606/40, 41, 48
See application file for complete search history.

(56) References Cited

U.S. PATENT DOCUMENTS

| | | | |
|---|---|---|---|
| 2,031,682 A | | 2/1936 | Frederick et al. |
| 4,074,718 A | | 2/1978 | Morrison, Jr. et al. |
| 4,375,220 A | | 3/1983 | Matvias |
| 4,411,266 A | | 10/1983 | Cosman |
| 4,565,200 A | * | 1/1986 | Cosman ...................... 600/373 |
| 4,576,177 A | * | 3/1986 | Webster, Jr. ................ 600/439 |
| 4,608,977 A | * | 9/1986 | Brown ........................ 606/130 |
| 4,662,383 A | * | 5/1987 | Sogawa et al. ............. 607/133 |
| 4,739,759 A | | 4/1988 | Rexroth et al. |
| 4,832,024 A | * | 5/1989 | Boussignac et al. ............ 606/7 |
| 4,880,719 A | * | 11/1989 | Murofushi et al. ........ 430/108.6 |
| 4,961,435 A | * | 10/1990 | Kitagawa et al. ............ 607/138 |
| 4,966,597 A | * | 10/1990 | Cosman ........................ 606/50 |
| 4,993,430 A | * | 2/1991 | Shimoyama et al. ........... 607/99 |
| 5,029,588 A | * | 7/1991 | Yock et al. .................. 600/471 |
| 5,103,804 A | * | 4/1992 | Abele et al. ................. 600/116 |
| 5,225,741 A | | 7/1993 | Auld, Jr. et al. |
| 5,230,623 A | * | 7/1993 | Guthrie et al. ................. 433/72 |
| 5,233,515 A | | 8/1993 | Cosman |
| 5,246,438 A | | 9/1993 | Langberg |

(Continued)

FOREIGN PATENT DOCUMENTS

DE 2407559 * 2/1974

(Continued)

OTHER PUBLICATIONS

Cosman Er, Cosman BJ; "Methods of Making Nervous System Lesions", in William RH, Rengachary SS (eds): Neurosurgery, New York, McGraw-Hill, vol. 111, pp. 2490-2498, 1984.*

(Continued)

Primary Examiner—Michael Peffley
Assistant Examiner—Ronald Hupczey, Jr.

(57) ABSTRACT

An ablation system includes an ablation electrode assembly operatively connectable to sources of electrosurgical energy and cooling fluid. The electrode assembly includes a hub defining a chamber therein; at least one electrically conductive ablation needle extending from the hub, the ablation needle including a distal end portion configured to penetrate tissue, said distal end portion being electrically and thermally conductive for establishing electric and thermal communication with the tissue; a heat sink operatively connected to the ablation needle, the heat sink being connected to the ablation needle to draw energy away from at least the distal end portion thereof, the heat sink including a proximal end extending into the chamber of the hub; and a conduit fluidly connected to the hub for delivering fluid into the chamber thereof from the source of fluid, wherein the fluid withdraws energy from the proximal end of the heat sink.

27 Claims, 3 Drawing Sheets

U.S. PATENT DOCUMENTS

| | | | |
|---|---|---|---|
| 5,267,994 A * | 12/1993 | Gentelia et al. | 606/15 |
| 5,281,213 A * | 1/1994 | Milder et al. | 606/15 |
| 5,323,778 A * | 6/1994 | Kandarpa et al. | 600/411 |
| 5,330,470 A | 7/1994 | Hagen | |
| 5,330,518 A * | 7/1994 | Neilson et al. | 607/101 |
| 5,334,193 A * | 8/1994 | Nardella | 606/41 |
| 5,342,357 A * | 8/1994 | Nardella | 606/40 |
| 5,348,554 A * | 9/1994 | Imran et al. | 606/41 |
| 5,370,675 A * | 12/1994 | Edwards et al. | 607/101 |
| 5,383,876 A * | 1/1995 | Nardella | 606/49 |
| 5,383,917 A * | 1/1995 | Desai et al. | 607/102 |
| 5,385,148 A * | 1/1995 | Lesh et al. | 600/471 |
| 5,403,311 A * | 4/1995 | Abele et al. | 606/49 |
| 5,409,000 A * | 4/1995 | Imran | 600/374 |
| 5,409,006 A * | 4/1995 | Buchholtz et al. | 600/439 |
| 5,417,686 A * | 5/1995 | Peterson et al. | 606/25 |
| 5,433,739 A * | 7/1995 | Sluijter et al. | 607/99 |
| 5,437,662 A * | 8/1995 | Nardella | 606/40 |
| 5,458,597 A * | 10/1995 | Edwards et al. | 606/41 |
| 5,462,521 A * | 10/1995 | Brucker et al. | 604/20 |
| 5,472,441 A * | 12/1995 | Edwards et al. | 606/41 |
| 5,490,850 A * | 2/1996 | Ellman et al. | 606/45 |
| 5,500,012 A * | 3/1996 | Brucker et al. | 607/122 |
| 5,520,684 A * | 5/1996 | Imran | 606/41 |
| 5,536,267 A * | 7/1996 | Edwards et al. | 606/41 |
| 5,571,147 A | 11/1996 | Sluijter et al. | |
| 5,588,432 A * | 12/1996 | Crowley | 600/439 |
| 5,599,345 A * | 2/1997 | Edwards et al. | 606/41 |
| 5,643,197 A | 7/1997 | Brucker et al. | |
| 5,647,871 A * | 7/1997 | Levine et al. | 606/45 |
| 5,662,111 A | 9/1997 | Cosman | |
| 5,688,267 A * | 11/1997 | Panescu et al. | 606/41 |
| 5,735,847 A | 4/1998 | Gough et al. | |
| 5,775,338 A | 7/1998 | Hastings | |
| 5,792,146 A | 8/1998 | Cosman | |
| 5,848,967 A | 12/1998 | Cosman | |
| 5,849,011 A | 12/1998 | Jones et al. | |
| 5,868,740 A * | 2/1999 | LeVeen et al. | 606/41 |
| 5,921,982 A * | 7/1999 | Lesh et al. | 606/41 |
| 5,943,719 A | 8/1999 | Feldman et al. | |
| 5,951,546 A | 9/1999 | Lorentzen | |
| 6,001,093 A | 12/1999 | Swanson et al. | |
| 6,006,126 A | 12/1999 | Cosman | |
| 6,053,912 A * | 4/2000 | Panescu et al. | 606/40 |
| 6,059,780 A * | 5/2000 | Gough et al. | 606/42 |
| 6,061,551 A | 5/2000 | Sorrells et al. | |
| 6,074,389 A * | 6/2000 | Levine et al. | 606/45 |
| 6,080,149 A | 6/2000 | Huang et al. | |
| 6,106,524 A | 8/2000 | Eggers et al. | |
| 6,132,426 A | 10/2000 | Kroll | |
| 6,146,380 A | 11/2000 | Racz et al. | |
| 6,162,216 A | 12/2000 | Guziak et al. | |
| 6,203,541 B1 | 3/2001 | Keppel | |
| 6,241,725 B1* | 6/2001 | Cosman | 606/41 |
| 6,246,912 B1 | 6/2001 | Sluijter et al. | |
| 6,287,305 B1 | 9/2001 | Heim et al. | |
| 6,306,132 B1 | 10/2001 | Moorman et al. | |
| 6,337,998 B1* | 1/2002 | Behl et al. | 607/101 |
| 6,432,070 B1 | 8/2002 | Talish et al. | |
| 6,478,793 B1 | 11/2002 | Cosman et al. | |
| 6,500,172 B1 | 12/2002 | Panescu et al. | |
| 6,503,248 B1* | 1/2003 | Levine | 606/45 |
| 6,506,189 B1 | 1/2003 | Rittman, III et al. | |
| 6,530,922 B2 | 3/2003 | Cosman et al. | |
| 6,575,969 B1 | 6/2003 | Rittman, III et al. | |
| 6,605,085 B1 | 8/2003 | Edwards | |
| 6,613,047 B2 | 9/2003 | Edwards | |
| 6,685,729 B2 | 2/2004 | Gonzalez | |
| 6,918,907 B2* | 7/2005 | Kelly et al. | 606/41 |
| 7,137,980 B2 | 11/2006 | Buysse et al. | |
| 7,156,842 B2 | 1/2007 | Sartor et al. | |
| 7,179,255 B2 | 2/2007 | Lettice et al. | |
| 7,186,222 B1 | 3/2007 | Callister et al. | |
| 7,207,989 B2 | 4/2007 | Pike, Jr. et al. | |
| 7,218,958 B2 | 5/2007 | Rashidi | |
| 7,235,070 B2 | 6/2007 | Vanney | |
| 7,235,073 B2* | 6/2007 | Levine et al. | 606/48 |
| 7,238,184 B2 | 7/2007 | Megerman et al. | |
| 7,264,619 B2 | 9/2007 | Venturelli | |
| 7,278,991 B2 | 10/2007 | Morris et al. | |
| 7,294,127 B2 | 11/2007 | Leung et al. | |
| 7,294,143 B2 | 11/2007 | Francischelli | |
| 7,302,285 B2 | 11/2007 | Fuimaono et al. | |
| 7,303,558 B2 | 12/2007 | Swanson | |
| 7,331,947 B2 | 2/2008 | McGuckin, Jr. et al. | |
| RE40,156 E | 3/2008 | Sharps et al. | |
| 7,341,586 B2 | 3/2008 | Daniel et al. | |
| 7,344,533 B2 | 3/2008 | Pearson et al. | |
| 7,364,578 B2 | 4/2008 | Francischelli et al. | |
| 7,364,579 B2 | 4/2008 | Mulier et al. | |
| 7,367,974 B2 | 5/2008 | Haemmerich et al. | |
| 7,367,975 B2 | 5/2008 | Malecki et al. | |
| 7,387,625 B2 | 6/2008 | Hovda et al. | |
| 7,419,486 B2 | 9/2008 | Kampa | |
| 7,419,487 B2 | 9/2008 | Johnson et al. | |
| 7,419,488 B2 | 9/2008 | Ciarrocca et al. | |
| 7,419,489 B2 | 9/2008 | Vanney et al. | |
| 7,422,587 B2 | 9/2008 | Bek et al. | |
| 2001/0034518 A1 | 10/2001 | Edwards et al. | |
| 2002/0058933 A1 | 5/2002 | Christopherson et al. | |
| 2002/0111615 A1 | 8/2002 | Cosman et al. | |
| 2002/0120261 A1 | 8/2002 | Morris et al. | |
| 2002/0156472 A1 | 10/2002 | Lee et al. | |
| 2003/0018247 A1 | 1/2003 | Gonzalez | |
| 2004/0002745 A1 | 1/2004 | Fleming et al. | |
| 2004/0039429 A1 | 2/2004 | Daniel et al. | |
| 2004/0181216 A1 | 9/2004 | Kelly et al. | |
| 2004/0199161 A1 | 10/2004 | Truckai et al. | |
| 2004/0254573 A1 | 12/2004 | Dycus | |
| 2004/0267256 A1 | 12/2004 | Garabedian et al. | |
| 2005/0096681 A1 | 5/2005 | Desinger et al. | |
| 2005/0107784 A1 | 5/2005 | Moses | |
| 2005/0107785 A1 | 5/2005 | Dycus | |
| 2005/0113824 A1 | 5/2005 | Sartor et al. | |
| 2005/0119655 A1 | 6/2005 | Moses | |
| 2005/0154387 A1 | 7/2005 | Moses | |
| 2005/0155743 A1* | 7/2005 | Getz et al. | 165/80.3 |
| 2005/0192564 A1 | 9/2005 | Cosman et al. | |
| 2006/0079885 A1 | 4/2006 | Rick et al. | |
| 2006/0079886 A1 | 4/2006 | Orszulak | |
| 2006/0079887 A1 | 4/2006 | Buysse | |
| 2007/0260240 A1 | 11/2007 | Rusin | |
| 2008/0021448 A1 | 1/2008 | Orszulak | |
| 2008/0027424 A1 | 1/2008 | DeCarlo et al. | |
| 2008/0183165 A1 | 7/2008 | Buysse et al. | |

FOREIGN PATENT DOCUMENTS

| | | | |
|---|---|---|---|
| DE | 24075594 | | 2/1974 |
| DE | 10224154 | | 12/2003 |
| EP | 0171967 A | | 2/1986 |
| EP | 0246350 | * | 11/1987 |
| EP | 0310431 | * | 4/1989 |
| EP | 0508609 | * | 8/1994 |
| EP | 1 070 518 A2 | | 1/2001 |
| EP | 05021939 A | | 10/2004 |
| EP | 1645234 | | 4/2006 |
| EP | 1656900 | | 5/2006 |
| FR | 2864439 | | 7/2005 |
| WO | WO 94/28809 | * | 12/1994 |
| WO | WO 96/04860 | * | 2/1996 |
| WO | WO 96/18349 | * | 8/1996 |
| WO | WO 96/29946 | * | 8/1996 |
| WO | WO 96/34571 | | 11/1996 |

| | | | |
|---|---|---|---|
| WO | WO 96/39914 | * | 12/1996 |
| WO | WO 97/06739 | * | 2/1997 |
| WO | WO 97/06740 | * | 2/1997 |
| WO | WO 97/06855 | * | 2/1997 |
| WO | WO 97/17029 | * | 5/1997 |
| WO | WO 99/01074 | | 1/1999 |
| WO | WO 99/04710 | * | 2/1999 |
| WO | WO 99/22657 | | 5/1999 |
| WO | WO 00/67846 | | 11/2000 |
| WO | WO 93/24066 | * | 12/2003 |
| WO | WO 01/00114 A1 | | 1/2004 |
| WO | WO 2004/045436 | | 6/2004 |
| WO | WO 2005/009528 | | 2/2005 |

OTHER PUBLICATIONS

Anderson, Gary et al, "A Numerical Study of Rapid Heating for High Temperature Radio Frequency Hyperthermia", International Journal of Bio-Medical COmputing, 35 (1994), 297-307.*

Goldberg et al, "Tissue Ablation with Radiofrequency: Effective Probe Size, Gauge, Duration and Temperature and Lesion Volume", Aced Radio, 1995, vol. 2, No. 5, pp. 399-404.*

Melvin A. Astrahan, "A Localized Current Field Hyperthermia System for Use with 192-Iridium Interstitial Implants", Medical Physics, 9(3), May/Jun. 1982.*

European Search Report from Application EP 05021935.

International Search Report from EP 05021025.1 dated Mar. 13, 2006.

European Search Report from Application EP 07009028 dated Jul. 16, 2007.

European Search Report from Application EP 05025423.4 dated Jan. 12, 2007.

Bulletin of the American Physical Society, vol. 47, No. 5, Aug. 2002.

European Search Report from Application EP 06019768 dated Jan. 8, 2007.

European Search Report from Application EP 05025424 dated Jan. 23, 2007.

Cosman et al. "Theoretical Aspects of Radiofrequency Lesions in the Dorsal Root Entry Zone". Neurosurgery 15:945-950, 1984.

Stuart W. Young, Nuclear Magnetic Resonance Imaging—Basic Principles, Raven Press, New York, 1984.

E.R. Cosman, et al., "Radiofrequency Lesion Generation and its Effect on Tissue Impedance", Applied Neurophysiology, 51:230-242, 1988.

K. Ogata, Modern Control Engineering, Prentice-Hall, Englewood Cliffs, N.J., 1970.

E. Alexander et al., "Magnetic resonance image-directed stereotactic neurosurgery: use of image fusion with computerized tomography to enhance spatial accuracy", J. Neurosurg., 83:271, 276, 1995.

Reidenbach (1995) "First Experimental Results with Special Applicators for High-Frequency Interstitial Thermotherapy", Society Minimally Ivasive Therapy, 4(Suppl 1) :40 (Abstr).

Organ LW. (1976) "Electrophysiologic Principles of Radiofrequency Lesion Making" Appl. Neurophysiol, vol. 39: pp. 69-76.

Livraghi et al. (1995) "Saline-enhanced RF Tissue Ablation in the Treatment of Liver Metastases", Radiology, 205-210.

Solbiati et al. (1995) "Percutaneous US-guided RF Tissue Ablation of Liver Metastases: Long-term Follow-up", Radiology, 197(P): 199.

Solbiati, et al. (2001) "Percutaneous Radio-frequency Ablation of Hepatic Metastases from Colorectal Cancer: Long-term Results in 117 Patients", *Radiology*, vol. 221, pp. 159-166.

Goldberg, et all., "Image-guided Radiofrequency Tumor Ablation: Challenges and Opportunities—Part 1", (2001) *J Vasc. Interv. Radiol*, vol. 12, pp. 1021-1032.

McGahan et al. (1995) "Percutaneous Ultrasound-guided Radiofrequency Electrocautery Ablationof Prostate Tissue in Dogs", Acad Radiol, vol. 2, No. 1:pp. 61-65.

Goldberg et al. (1995) "Tissue Ablation with Radiofrequency Using Multiprobe Arrays", Acad Radiol, vol. 2: pp. 399-404.

Goldberg et al. (1995) "Saline-enhanced RF Ablation: Demonstration of Efficacy and Optimization of Parameter", Radiology, 197(P): 140 (Abstr).

European Search Report from Application EP 05021936.9 dated Feb. 6, 2006.

European Search Report from Application EP 05021939.

McRury, Ian D., (2000) "The Effect of Ablation Sequence and Duration on Lesion Shape Using Rapidly Pulsed Radiofrequency Energy Through Electrodes", Springer Netherlands, vol. 4, No. 1, pp. 307-320.

* cited by examiner

COOLED RF ABLATION NEEDLE

BACKGROUND

1. Technical Field

The present disclosure relates to advances in medical systems and procedures for prolonging and improving human life and, more particularly, to novel electrosurgical instruments for tissue ablation, systems for tissue ablation including the electrosurgical instruments, and methods for ablating tissues containing abnormalities such as cancerous tumors using the systems for tissue ablation.

2. Discussion of Related Art

Therapeutic lesions in living bodies have been accomplished for many decades using radio-frequency (RF) and other forms of energy. The procedures have been particularly useful in the field of neurosurgery, typically where RF-ablation electrodes (usually of elongated cylindrical geometry) are inserted into a living body. A typical form of such ablation electrodes incorporates an insulated sheath from which an exposed (uninsulated) tip extends.

Generally, the ablation electrode is coupled between a grounded RF power source, e.g., an electrosurgical generator, (outside the body) and a reference ground or indifferent electrode, e.g., return electrode, for contacting a large surface of the body. When an RF voltage is provided between the ablation electrode and the reference ground, RF current flows from the ablation electrode through the body. Typically, the current density is very high near the tip of the ablation electrode, which heats and destroys the adjacent tissue.

In the past, RF ablation electrodes have incorporated temperature sensors, for example, in the form of a thermistor or thermocouple as disclosed in U.S. Pat. No. 4,411,266 to Cosman. Typically, the sensor is connected to a monitoring apparatus for indicating temperature to assist in accomplishing a desired lesion. As generally known, for a given tip geometry and tip temperature, lesions of a prescribed size can be made quite consistently, also disclosed in U.S. Pat. No. 4,411,266 to Cosman.

Over the years, a wide variety of RF electrode shapes and configurations have been used, for example, several current forms are available from Radionics, Inc., located in Burlington, Mass. Such electrodes have been used to accomplish lesions in a wide variety of targets within the body, including the brain, the spinal column and the heart.

An important criterion when using electrode ablation systems relates to the temperature of the tip achieved during the ablation process. Specifically, it is desirable to maintain the temperature of certain ablation electrodes, of a given tip geometry, below 100° C. At a temperature at or above 100° C., the tissue surrounding the ablation electrode will tend to boil and char. Consequently, the lesion size for a given electrode geometry generally has been considered to be somewhat limited by the fact that the tissue near the tip must not exceed 100° C.

Essentially, during RF ablation, the electrode temperature is highest near the tip, because the current density is the highest at that location. Accordingly, temperature falls off as a function of distance from the electrode tip and, except for possible abnormalities in tissue conductivity and so on, in a somewhat predictable and even calculable pattern. As an attendant consequence, the size of RF lesions for a given electrode geometry have been somewhat limited.

One proposed solution to the limitation of lesion's size has been to employ "off-axis" electrodes, for example the so called Zervas Hypophysectomy Electrode or the Gildenberg Side-Outlet electrode, as manufactured by Radionics, Inc., Burlington, Mass. However, such systems, in requiring multiple tissue punctures, increase trauma to the patient.

Considering lesion size, it has been seen that lesions in the brain of up to 10 to 12 millimeters, by using very large ablation electrodes, may be produced. However, in order to produce similarly sized lesions or larger sized lesions with relatively smaller ablation electrodes, ablations systems including ablation electrodes with conduits which deliver cooling fluid to the tip thereof have been developed. Reference may be made to U.S. Pat. Nos. 5,951,546; 6,506,189; 6,530,922; and 6,575,969, the entire contents of each of which being incorporated herein by reference, for a detailed discussion of such systems. Generally, ablation electrodes with cooled conductive tips produce larger lesion volumes as compared to ablation tips which are not cooled.

Accordingly, a need exists for electrosurgical instruments for tissue ablation, systems for tissue ablation including the electrosurgical instruments, and method for ablating tissues containing abnormalities such as cancerous tumors using the systems for tissue ablation.

SUMMARY

The present disclosure relates to novel electrosurgical instruments for tissue ablation, systems for tissue ablation including the electrosurgical instruments, and methods for ablating tissues containing abnormalities such as cancerous tumors using the systems for tissue ablation.

According to an aspect of the present disclosure, an ablation system is provided. The ablation system includes an ablation electrode assembly operatively connectable to a source of electrosurgical energy and to a source of cooling fluid. The ablation electrode assembly includes a hub defining a chamber therein; at least one electrically conductive ablation needle extending from the hub, the ablation needle including a distal end portion configured to penetrate tissue, said distal end portion being electrically and thermally conductive for establishing electric and thermal communication with the tissue; a heat sink operatively connected to the ablation needle, the heat sink being connected to the ablation needle to draw energy away from at least the distal end portion thereof, the heat sink including a proximal end extending into the chamber of the hub; and a conduit fluidly connected to the hub for delivering fluid into the chamber thereof from the source of fluid, wherein the fluid withdraws energy from the proximal end of the heat sink.

The heat sink may be fabricated from a conductive material which is anisotropic, such as, for example, a graphite fiber.

The ablation system may further include an outlet conduit fluidly connected to the chamber of the hub for delivering fluid from the chamber thereof.

The ablation needle may define a cavity therein. The heat sink may be disposed within the cavity of the ablation needle. The cavity of the ablation needle may extend to the distal end portion of thereof. Accordingly, a distal end of the heat sink may be in conductive engagement with a distal end surface of the cavity of the ablation needle.

The ablation system may further include an insulative coating surrounding at least a portion of a length of the ablation needle. The distal end portion of the ablation needle may be exposed.

It is envisioned that the heat sink may encase at least a portion of a length of the ablation needle. Desirably, the distal end portion of the ablation needle is exposed. In an embodiment, an insulative coating may surround at least a portion of a length of the heat sink encasing the ablation needle.

The ablation system may further include a source or electrosurgical energy electrically connected to the ablation needle. The ablation system may still further include a source of cooling fluid fluidly connected to the chamber of the hub. The ablation system may further include a thermal-sensing circuit electrically connected to the ablation needle for measuring a temperature of the ablation needle. The ablation system may further include a microprocessor connected to and for coordinating operation of the source of electrosurgical energy and the source of fluid.

In an embodiment, it is envisioned that the ablation needle is solid. It is envisioned that a plurality of ablation needles may be provided.

According to a further aspect of the present disclosure, an ablation electrode assembly operatively connectable to a source of electrosurgical energy and to a source of cooling fluid is provided. The ablation electrode assembly includes a hub defining a chamber therein; at least one electrically conductive ablation needle extending from the hub, the ablation needle including a distal end portion configured to penetrate tissue, said distal end portion being electrically and thermally conductive for establishing electric and thermal communication with the tissue; a heat sink operatively connected to the ablation needle, the heat sink being connected to the ablation needle to draw energy away from at least the distal end portion thereof, the heat sink including a proximal end extending into the chamber of the hub; and a conduit fluidly connected to the hub for delivering fluid into the chamber thereof from the source of fluid, wherein the fluid withdraws energy from the proximal end of the heat sink.

The heat sink may be fabricated from a conductive material including an anisotropic material, such as, for example, a graphite fiber.

The ablation electrode assembly further includes an outlet conduit fluidly connected to the chamber of the hub for delivering fluid from the chamber thereof.

The ablation needle may define a cavity therein. The heat sink may be disposed within the cavity of the ablation needle. The cavity of the ablation needle may extend to the distal end portion thereof. Accordingly, a distal end of the heat sink may be in conductive engagement with a distal end surface of the cavity of the ablation needle.

The ablation electrode may further include an insulative coating surrounding at least a portion of a length of the ablation needle. The distal end portion of the ablation needle desirably remains exposed.

In an embodiment, it is envisioned that the heat sink encases at least a portion of a length of the ablation needle. In this embodiment, desirably, the distal end portion of the ablation needle remains exposed. It is envisioned that an insulative coating may surround at least a portion of a length of the heat sink encasing the ablation needle.

The ablation electrode assembly may further include a thermal-sensing circuit electrically connected to the ablation needle for measuring a temperature of the ablation needle.

The ablation needle may be solid. It is envisioned that a plurality of ablation needles may be provided.

According to yet another aspect of the present disclosure, a method for heat ablation of tissue in a patient is provided. The method includes the step of providing an ablation electrode assembly for tissue ablation. The ablation electrode assembly includes a hub defining a chamber therein; at least one electrically conductive ablation needle extending from the hub, the ablation needle including a distal end portion configured to penetrate tissue, said distal end portion being electrically and thermally conductive for establishing electric and thermal communication with the tissue; a heat sink operatively connected to the ablation needle, the heat sink being connected to the ablation needle to draw energy away from at least the distal end portion thereof, the heat sink including a proximal end extending into the chamber of the hub; and a conduit fluidly connected to the hub for delivering fluid into the chamber thereof from a source of fluid, wherein the fluid withdraws energy from the proximal end of the heat sink.

The method further includes the steps of inserting the ablation needle into the tissue to a target surgical site; supplying electrical energy to the distal end portion of the ablation needle to effect tissue ablation proximate the distal end portion; and cooling the distal end portion of the ablation needle by circulating fluid around the proximal end of the heat sink extending into the chamber of the hub.

The method may further include the step of providing the heat sink within a cavity defined in the ablation needle.

The method may further include the step of providing an insulative coating over a substantial length of the ablation needle to prevent ablation of tissue in the body of a patient contiguous to the insulative coating.

The method may still further include the step of providing at least one of a source or electrosurgical energy electrically connected to the ablation needle; a source of cooling fluid fluidly connected to the chamber of the hub; a thermal-sensing circuit electrically connected to the ablation needle for measuring a temperature of the ablation needle; and a microprocessor connected to and for coordinating operation of the source of electrosurgical energy and the source of fluid.

The method may further include the step of providing a plurality of ablation needles.

According to still another aspect of the present disclosure, an ablation system is provided including an ablation electrode assembly operatively connectable to at least one of a source of electrosurgical energy and a source of cooling fluid. The ablation electrode assembly includes at least one electrically conductive ablation needle having a distal end portion configured to penetrate tissue, wherein said distal end portion is electrically and thermally conductive for establishing electric and thermal communication with the tissue; and a heat sink operatively connected to the ablation needle, wherein the heat sink is connected to the ablation needle to draw energy away from at least the distal end portion thereof. The heat sink includes a proximal end extending proximally of the ablation needle.

The ablation electrode assembly further includes a hub defining a chamber therein. Accordingly, the ablation needle extends from the hub and the proximal end of the heat sink extends into the chamber of the hub.

The ablation system may further include a conduit fluidly connected to the hub for delivering fluid into the chamber thereof from the source of fluid, wherein the fluid withdraws energy from the proximal end of the heat sink.

BRIEF DESCRIPTION OF THE DRAWINGS

Further features and advantages of the invention will become readily apparent from the following specification and from the drawings, in which.

DETAILED DESCRIPTION OF EMBODIMENTS

Figures 1, 2, 3:
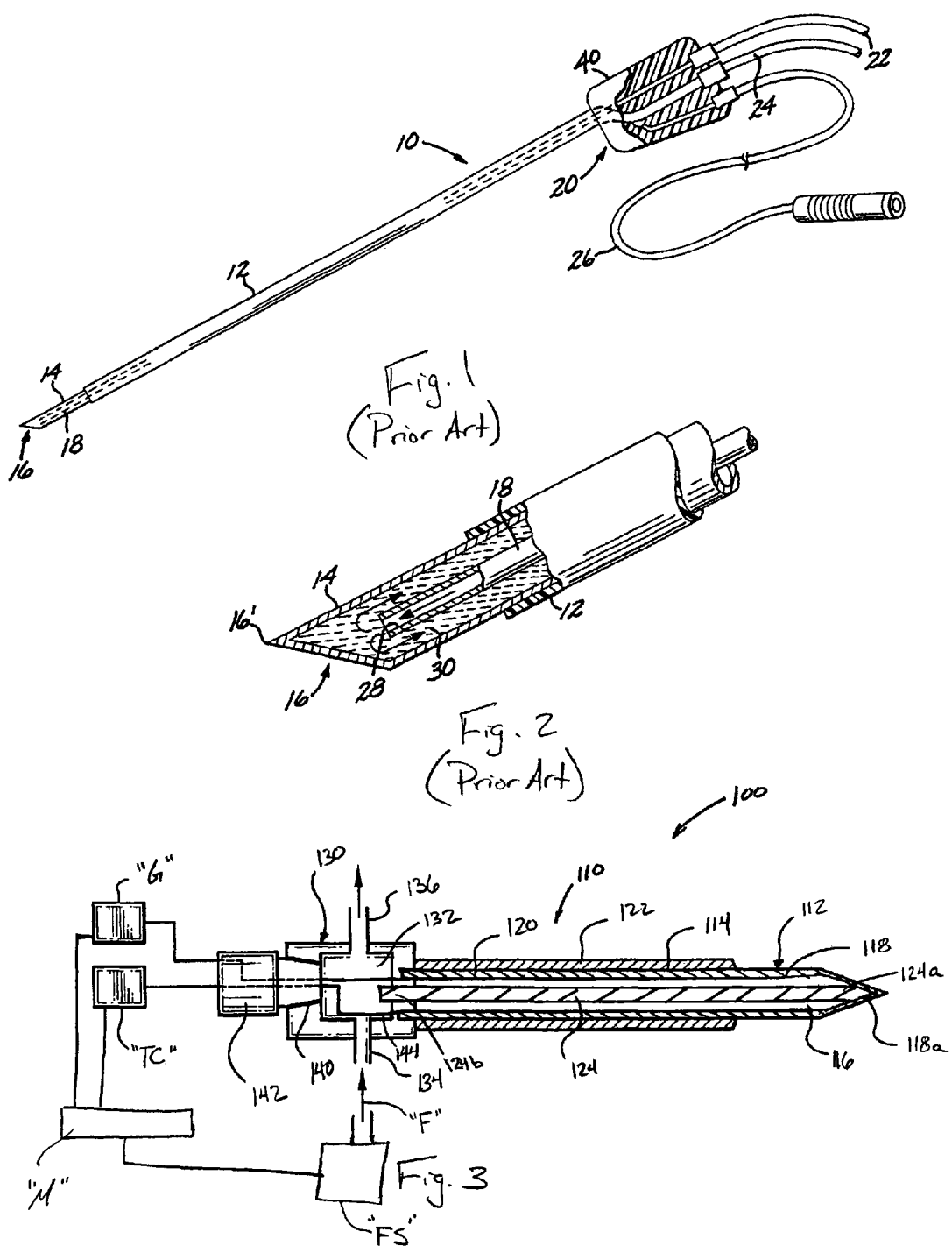
FIG. 1 is a partial cross-sectional view of a prior art cooled needle electrode.
FIG. 2 is a broken-away partial cross-sectional view of the tip part of the cooled needle electrode of FIG. 1.
FIG. 3 is a schematic, partial cross-sectional illustration, of an ablation system in accordance with an embodiment of the present disclosure.

Referring initially to FIGS. 1 and 2, a prior art needle electrode according is shown and described and is generally designated as 10. As seen in FIG. 1, needle electrode 10 includes a distal end 16 and a proximal end 20 and further includes an outer tube 14 having a tip part 16 which is exposed and a tip point 16' (see FIG. 2) which is construed so as to penetrate tissue with a minimum risk of hemorrhage from the puncture tract. The non-exposed part of the outer tube 14 is surrounded by an insulating material 12. A distal portion of outer tube 14 is non-insulated and thereby exposed for DC or AC, preferably RF delivery. An inner tube 18 is provided inside the tube 14 co-axially with the outer tube 14.

An adapter 40 is provided at the proximal end 20 of needle electrode 10, opposite the tip part or distal end 16. The adapter 40 is equipped with a line 22, the line 22 being connected to the inner tube 18 and communicating therewith for providing a cooling fluid, such as water, to the distal end 16 of needle electrode 10. The water is led through the inner tube 18 to the tip part 16 and away from the tip part through the interior of the outer tube 14. The outer tube 14 is connected to and communicates with a line 24 for discharge of the cooling water. Lines 22 and 24 each communicate with a cooling water reservoir (not shown). Circulation of the cooling water is established with a pump (not shown). The outer tube 14 of the cooled needle electrode 10 is connected to a RF electrosurgical generator (not shown) through line 26 for providing power to the cooled needle electrode 10.

In FIG. 2, the tip part or distal end 16 of the cooled needle electrode 10 of FIG. 1 is shown. As seen in FIG. 2, the cooling water flows through the inner tube 18 and out at a tip 28 of the inner tube 18 and flows into the tip part 16 and out of the outer tube 14 shown at 30 for thereby providing a cooled needle electrode 10.

Preferred embodiments of the presently disclosed ablation system will now be described in detail with reference to the drawing figures wherein like reference numerals identify similar or identical elements. As used herein, the term "distal" refers to that portion which is further from the user while the term "proximal" refers to that portion which is closer to the user.

Figure 4:
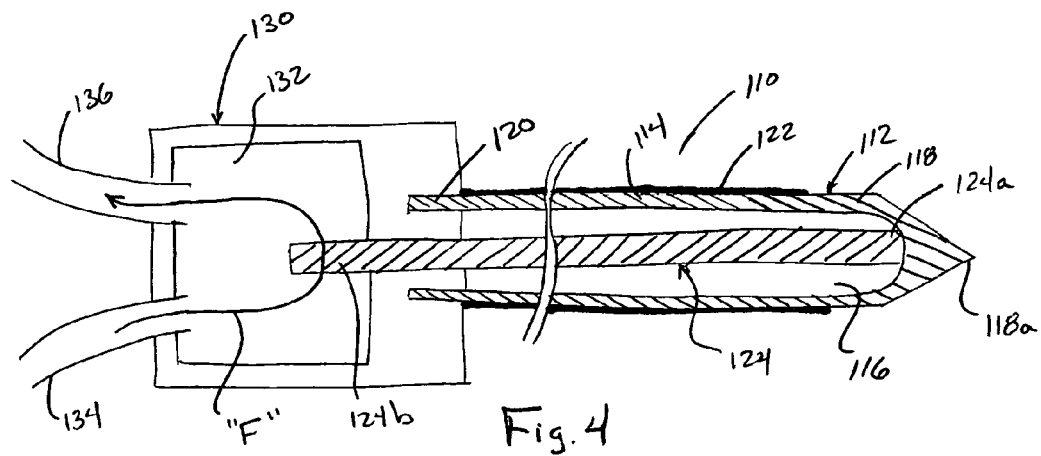
FIG. 4 is a schematic, partial cross-sectional illustration, of an embodiment of an ablation electrode assembly of the ablation system of FIG. 3.

Referring now to FIGS. 3 and 4, an ablation system, in accordance with an embodiment of the present disclosure, is shown generally as 100. Ablation system 100 includes an ablation electrode assembly 110 operatively connected to an electrosurgical energy source "G" (e.g., an electrosurgical generator), and a source of cooling fluid "FS". A microprocessor or computer "M" may be connected to energy source "G" and fluid source "FS" for controlling and monitoring the operating parameters of ablation system 100.

As seen in FIGS. 3 and 4, ablation electrode assembly 110 includes an elongate ablation needle 112 which is configured and dimensioned for insertion into a patient, either percutaneously or intraoperatively. Ablation needle 112 includes a substantially cylindrical body or shaft portion 114 defining a cavity or chamber 116 therein. Ablation needle 112 includes a distal end portion 118 having a sharpened tip 118a, and a proximal end portion 120 configured and adapted for connection to a hub 130 or the like. Desirably, ablation needle 112 is fabricated from electrically conductive material, such as, for example, stainless steel, titanium, etc.

Ablation electrode assembly 110 has an insulative coating 122 over at least a portion of the length of ablation needle 112, preferably, over most of the length of ablation needle 112. Desirably, insulative coating 122 extends from hub 130 to distal end portion 118 of ablation needle 112, such that distal end portion 118 of ablation needle 112 is exposed or un-insulated. Insulative coating 122 selectively prevents the flow of electrical current from shaft portion 114 of ablation needle 112 into surrounding tissue. Thus, insulative coating 122 shields the intervening tissue from RF current, so that such tissue is not substantially heated along the length of shaft portion 114 except by the heating effect from distal end portion 118 which is exposed.

Ablation electrode assembly 110 further includes at least one heat sink, in the form of heat strap or heat pipe 124 extending through cavity 116 of ablation needle 112. While a single heat strap 124 is shown and will be described, it is envisioned and within the scope of the present disclosure for a plurality of heat straps 124 to be provided. Heat strap 124 includes a distal end 124a operatively secured to ablation needle 112 and a proximal end 124b extending into a cavity 132 formed in hub 130. In the present embodiment, distal end 124a of heat strap 124 is operatively connected or secured to distal end portion 118 of ablation needle 112. In an embodiment, distal end 124a of heat strap 124 is bonded to distal end portion 118 of ablation needle 112 with a thermally conductive adhesive or the like.

Heat strap 124 is fabricated from a highly heat conductive anisotropic material, such as, for example, graphite fiber. Accordingly, in use, as will be described in greater detail below, heat strap 124 draws heat away from distal end portion 118 of ablation needle 112 and dissipates the heat along a length thereof. In order to increase the efficiency and the rate of heat dissipation, as will be described in greater detail below, a cooling fluid may be circulated over proximal end 124b of heat strap 124.

As seen in FIG. 3, ablation system 100 further includes a hub 130 configured and adapted to support ablation electrode assembly 110. Hub 130 defines a chamber 132 therein, an inlet conduit 134 for delivering cooling fluid "F" into chamber 132 from fluid source "FS", and an outlet conduit 136 for delivering cooling fluid "F" from chamber 132. In operation, cooling fluid "F" is communicated into chamber 132 through inlet conduit 134 and out of chamber 132 through outlet conduit 136.

As mentioned above, with proximal end 124b of heat strap 124 extending into chamber 132 of hub 130, as cooling fluid "F" is circulated through chamber 132 of hub 130, heat or energy is withdrawn from proximal end 124b of heat strap 124 and carried away to fluid source "FS" for re-cooling and the like.

As seen in FIG. 3, hub 130 may include a proximal connector known as a luer connector, which is a tapered hole 140 or the like. Into female luer connector 140, a hub of a high frequency or thermo-sensing electrode 142 may be inserted and sealed by its male luer connection. A probe 144 of thermo-sensing electrode 142 may be connected to ablation needle 112 which can sense the temperature of ablation needle 112 at that point, or alternatively, may sense the temperature of distal end portion 118. Since distal end portion 118 of ablation needle 112 is contiguous and in contact on its external surface with the target tissue within the patient's body, thermo-sensing probe 144 can, depending on the thermal contact with ablation needle 112, get a measure of the temperature of the tissue immediately outside of distal end portion 118.

Connected to or within the hub of the high frequency and/or thermo-sensing electrode 142 are connections indicated by the dashed lines which connect to a high frequency electrosurgical generator "G" and/or a thermal-sensing circuit "TC" that may be outside of the body.

Electrosurgical generator "G" may be the source of high frequency voltage which produces the high frequency current that emanates from the distal end portion 118 of ablation needle 112. The thermal-sensing circuit "TC" may be of a thermocouple type and the temperature sensor could also be a bi-metal junction thermocouple such as a copper constantan.

Figure 5:
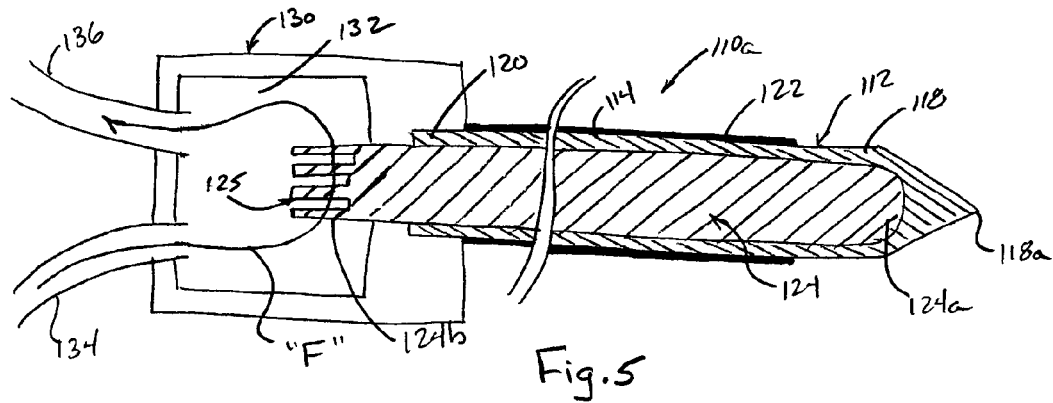
FIG. 5 is a schematic, partial cross-sectional illustration, of another embodiment of an ablation electrode assembly of the ablation system of FIG. 3.

Turning now to FIG. 5, an alternate embodiment of ablation electrode assembly is generally shown as 110a. Ablation electrode assembly 110a is substantially similar to ablation electrode assembly 110 and thus will only be discussed in detail to the extent necessary to identify differences in construction and/or operation. As seen in FIG. 5, heat strap 124 completely fills cavity 116 of ablation needle 112. In so doing, dissipation of heat and/or energy may take place along substantially the entire length of ablation needle 112.

As mentioned above with regard to ablation electrode assembly 110, with regard to ablation electrode assembly 110a, with proximal end 124b of heat strap 124 extending into chamber 132 of hub 130, as cooling fluid "F" is circulated through chamber 132 of hub 130, heat or energy is withdrawn from proximal end 124b of heat strap 124 and carried away to fluid source "FS" for re-cooling and the like. It is contemplated that proximal end 124b of heat strap 124 may include a plurality of fingers 125 or the like, thereby increasing the surface area over which fluid "F" is circulated and thus increasing the rate of heat and/or energy dissipation.

Figure 6:
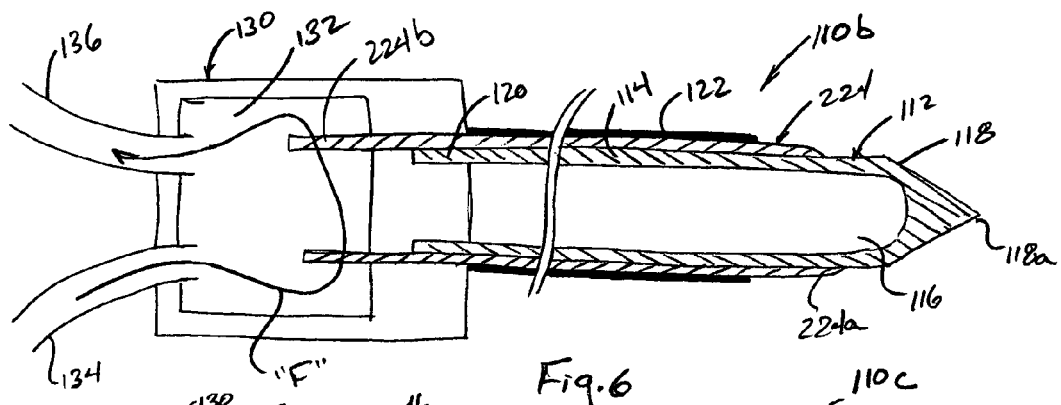
FIG. 6 is a schematic, partial cross-sectional illustration, of yet another embodiment of an ablation electrode assembly of the ablation system of FIG. 3.
Figure 7:
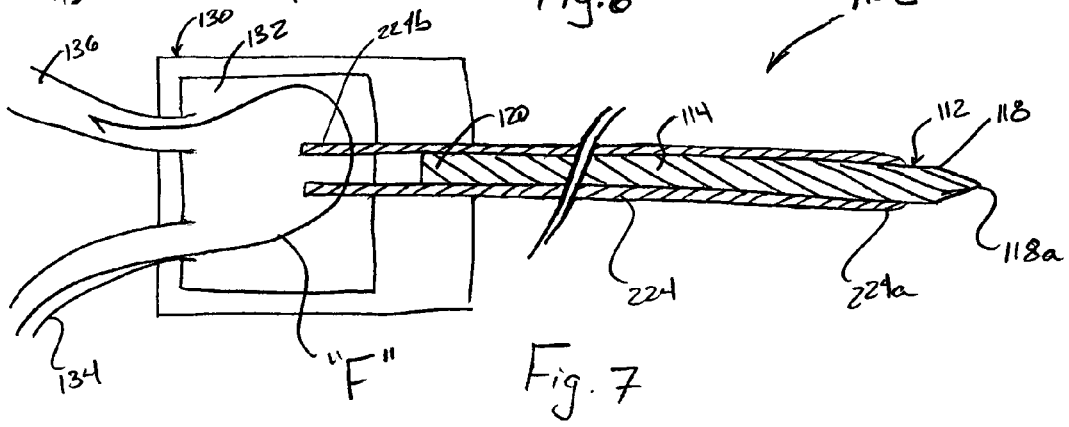
FIG. 7 is a schematic, partial cross-sectional illustration, of still another embodiment of an ablation electrode assembly of the ablation system of FIG. 3.

Turning now to FIGS. 6 and 7, alternate embodiments of ablation electrode assemblies are generally shown as 110b and 110c, respectively. Ablation electrode assemblies 110b, 110c are substantially similar to ablation electrode assembly 110 and thus will only be discussed in detail to the extent necessary to identify differences in construction and/or operation.

As seen in FIG. 6, ablation electrode assembly 110b includes a heat sink or heat strap, in the form of a sleeve or coating 224 wrapped around or surrounding at least a portion of the length of ablation needle 112, preferably over most of the length of ablation needle 112. Desirably, heat strap 224 extends to and not beyond distal end portion 118 of ablation needle 112, thus maintaining distal end portion 118 of ablation needle 112 exposed. Heat strap 224 includes a proximal end portion 224b which extends through hub 130 and into cavity 132.

In this embodiment, insulating coating 122 desirably encases and/or surrounds substantially all of heat strap 224. Alternatively, heat strap 224 may function as an insulating sleeve or barrier, thus eliminating the need for an insulating coating 122 disposed on or about heat strap 224.

As seen in FIG. 7, ablation electrode assembly 110c may include an ablation needle 112 which is solid (i.e., no cavity 116 is provided). In the present embodiment, heat strap 224 substantially encases ablation needle 112. Desirably, distal end portion 118 of ablation needle 112 remains exposed. Heat strap 224 includes a proximal end portion 224b which extends through hub 130 and into cavity 132. As with the embodiment in FIG. 6, heat strap 224 of the present embodiment also functions as an insulating coating or the like.

Desirably, distal end portion 118 of ablation needle 112 is exposed about 2.0 cm in length. Ablation needle 112 desirably has a transverse diameter of about 2 mm.

In operation, ablation electrode assembly 110 is inserted into an operative site of a patient, either percutaneously or intra-operatively. Desirably, ablation electrode assembly 110 is inserted into the operative site until distal end portion 118 of ablation needle 112 is positioned or disposed adjacent to or within a target tissue to be ablated. A return pad or return electrode (not shown) may know be or may previously have been operatively adhered to or connected to the patient. Any known technique may be used to visually position distal end portion 118 of ablation needle 112 in the operative site, such as, for example and not limited to, X-ray imaging, CT scanning, MRI's, fluoroscopy, angiographic, PET, SPECT, MEG, ultrasonic imaging, etc.

With distal end portion 118 of ablation needle 112 in position, electrosurgical energy is delivered from electrosurgical generator "G" to distal end portion 118 of ablation needle 112. Desirably, an effective amount of electrosurgical energy at an effective energy level and for an effective duration of time is delivered to distal end portion 118 of ablation needle 112 to treat and/or ablate the target tissue of the like. For example, electrosurgical generator "G" may deliver an energy frequency of from about 100 kilo Hertz to several hundred mega Hertz. An example of an electrosurgical generator "G" capable of producing such an output is the lesion generator available from Radionics, Inc, of Burlington, Mass.

Either prior to or simultaneously with the delivery of electrosurgical energy to distal end portion 118 of ablation needle 112, a fluid "F" (e.g., water, saline, etc.) is circulated through chamber 132 of hub 130. Desirably, fluid "F" is cooled to a temperature of about 0° C. prior to circulation. During circulation, fluid "F" enters chamber 132 of hub 130 through inlet conduit 134 and exits chamber 132 of hub 130 through outlet conduit 136. In so doing, fluid "F" contacts and/or washes over/across proximal end 124b or 224b of heat straps 124, 224, respectively, and withdraws heat and/or energy therefrom and, in turn, from ablation needle 112.

Following treatment or ablation of the target tissue, ablation electrode assembly 110 may be withdrawn from the target site and re-introduced into another target site, into the same target site from a different angle or approach, or in substantially the same location.

Figure 8:
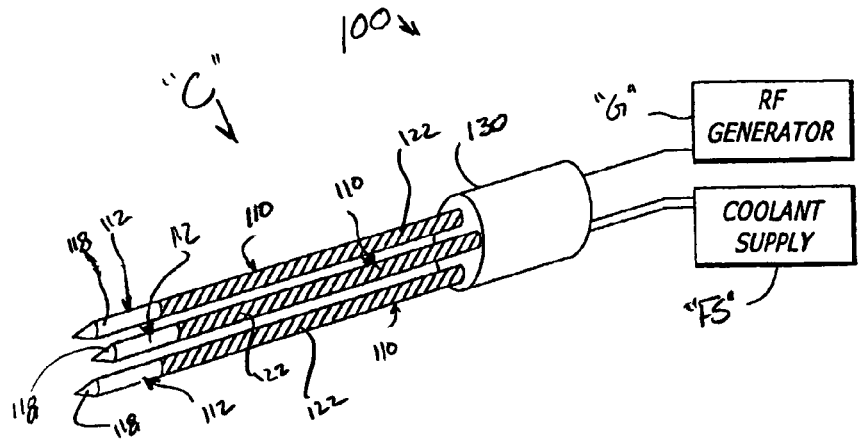
FIG. 8 is a schematic perspective view of an ablation system according to another embodiment of the present disclosure.
Figure 9:
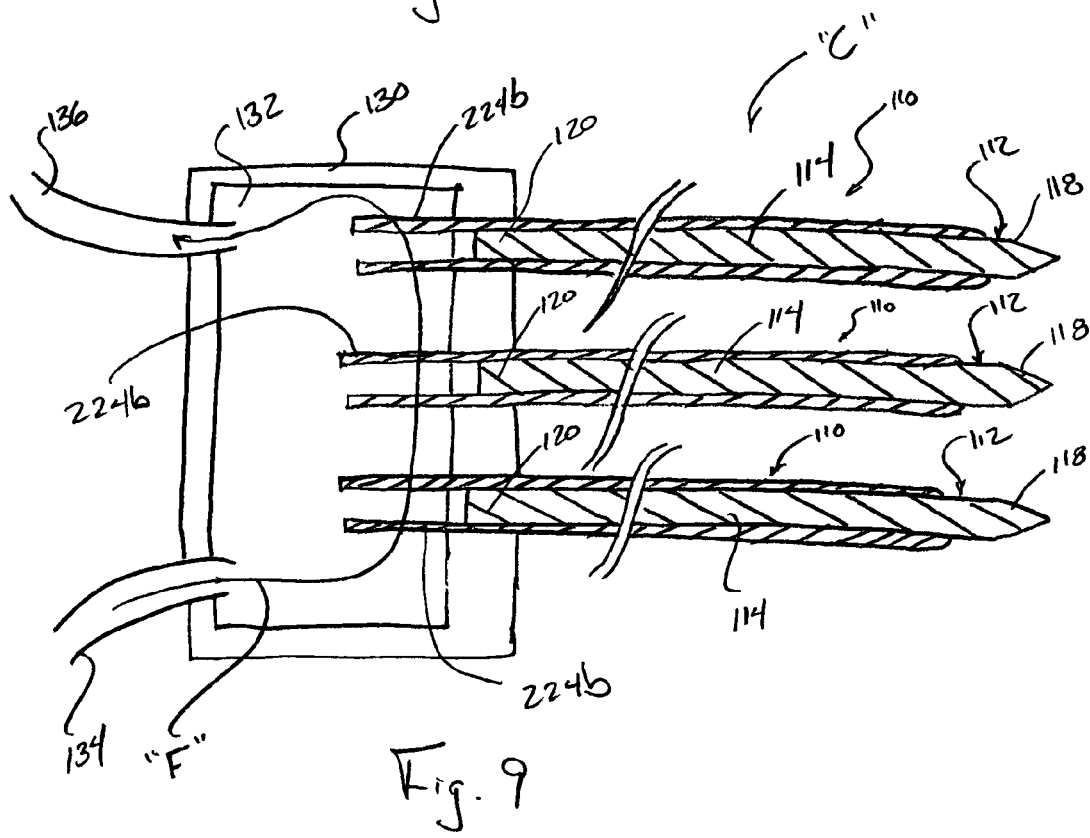
FIG. 9 is a schematic longitudinal cross-sectional view of the ablation system of FIG. 8.

Turning now to FIGS. 8 and 9, ablation system 100 may include a cluster "C" or plurality of ablation electrode assemblies 110 supported in hub 130. Desirably, any of ablation electrode assemblies 110-110c may be supported on or operatively connected to hub 130. Cluster "C" of ablation electrode assemblies 110 are each connected to electrosurgical generator "G". Accordingly, cluster "C" will effectively act as a larger electrode.

It is envisioned that ablation electrode assemblies 110 may be arranged in a substantially linear array, as shown in FIG. 9, or may be evenly spaced from one another, as shown in FIG. 8. While three ablation electrode assemblies 110 are shown and described, it is envisioned that any number of ablation electrode assemblies may be provided.

In use, as fluid "F" is circulated through chamber 132 of hub 130, fluid "F" circulates over or washes across proximal ends 224b of heat straps 224 of each ablation electrode assembly 110 extending into chamber 132 of hub 130. In so doing, heat and/or energy is/are drawn from each heat strap 224 and, in turn, from each ablation needle 112.

The use of a multiplicity of N ablation electrode assemblies 110 increases the overall conductive exposed tip area by which to send RF current for heating into the target tissue site. This increases the heating power that may be delivered and thus increases the size of the ablation volume possible.

The cooling capacity of a multiplicity of N ablation electrode assemblies also increases as the number N increases. Increasing the number of ablation electrode assemblies increases the cooling surface area near cluster "C". Thus, the heat sinking effect from a cluster of ablation electrode assemblies is greater than the heat sinking effect from a single ablation electrode assembly. This allows the size of a lesion to be expanded accordingly.

For example, in specific embodiments, ablation electrode assemblies 110 of cluster "C" may have diameters in the range of about 0.5 mm to about 3.0 mm. An advantage of a multiplicity of coherent smaller electrodes versus insertion of a single large electrode is that the smaller electrodes will produce less chance of hemorrhage.

Although the subject device, systems and methods have been described with respect to preferred embodiments, it will be readily apparent, to those having ordinary skill in the art to which it appertains, that changes and modifications may be made thereto without departing from the spirit or scope of the subject of the present disclosure.

What is claimed is:

1. An ablation system, comprising:
  a source of electrosurgical energy;
  a source of cooling fluid;
  an ablation electrode assembly operatively connected to the source of electrosurgical energy and to the source of cooling fluid, the ablation electrode assembly including:
    a hub defining a chamber therein;
    at least one electrically conductive ablation needle extending from the hub, the ablation needle including a sharpened distal end portion configured to penetrate tissue, said distal end portion being electrically and thermally conductive for establishing electric and thermal communication with the tissue;
    a heat sink operatively connected to the ablation needle, the heat sink being connected to the ablation needle to draw energy away from at least the distal end portion thereof, the heat sink including a proximal end extending into the chamber of the hub and a distal end extending substantially the length of the ablation needle, wherein the heat sink is fabricated from an anisotropic and conductive material;
  a first conduit fluidly connected to the hub for delivering fluid into the chamber thereof from the source of fluid; and
  a second conduit fluidly connected to the hub for draining fluid from the chamber thereof, wherein the hub is configured to direct the cooling fluid from the first conduit over the proximal end of the heat sink and out the second conduit to withdraw energy from the proximal end of the heat sink.

2. An ablation system, comprising:
  a source of electrosurgical energy;
  a source of cooling fluid;
  an ablation electrode assembly operatively connected to the source of electrosurgical energy and to the source of cooling fluid, the ablation electrode assembly including:
    a hub defining a chamber therein;
    at least one electrically conductive ablation needle extending from the hub, the ablation needle including a sharpened distal end portion configured to penetrate tissue, said distal end portion being electrically and thermally conductive for establishing electric and thermal communication with the tissue;
    a heat sink operatively connected to the ablation needle, the heat sink being connected to the ablation needle to draw energy away from at least the distal end portion thereof, the heat sink including a proximal end extending into the chamber of the hub and a distal end extending substantially the length of the ablation needle, wherein the heat sink is fabricated from a graphite fiber;
  a first conduit fluidly connected to the hub for delivering fluid into the chamber thereof from the source of fluid; and
  a second conduit fluidly connected to the hub for draining fluid from the chamber thereof, wherein the hub is configured to direct the cooling fluid from the first conduit over the proximal end of the heat sink and out the second conduit to withdraw energy from the proximal end of the heat sink.

3. The ablation system according to claim 2, wherein the ablation needle defines a cavity therein.

4. The ablation system according to claim 3, wherein the heat sink is disposed within the cavity of the ablation needle.

5. The ablation system according to claim 4, wherein the cavity of the ablation needle extends to the distal end portion thereof, and wherein a distal end of the heat sink is in conductive engagement with a distal end surface of the cavity of the ablation needle.

6. The ablation system according to claim 5, further comprising an insulative coating surrounding at least a portion of a length of the ablation needle.

7. The ablation system according to claim 6, wherein the distal end portion of the ablation needle is exposed.

8. The ablation system according to claim 2, wherein the heat sink encases at least a portion of a length of the ablation needle.

9. The ablation system according to claim 8, wherein the distal end portion of the ablation needle is exposed.

10. The ablation system according to claim 9, further comprising an insulative coating surrounding at least a portion of a length of the heat sink encasing the ablation needle.

11. The ablation system according to claim 9, further comprising a thermal-sensing circuit electrically connected to the ablation needle for measuring a temperature of the ablation needle.

12. The ablation system according to claim 11, wherein the ablation needle is solid.

13. The ablation system according to claim 12, further comprising a plurality of ablation needles.

14. The ablation system according to claim 13, further comprising a microprocessor connected to and for coordinating operation of the source of electrosurgical energy and the source of fluid.

15. An ablation electrode assembly operatively connectable to a source of electrosurgical energy and to a source of cooling fluid, the ablation electrode assembly comprising:
  a hub defining a chamber therein;
  at least one electrically conductive ablation needle extending from the hub, the ablation needle including a sharpened distal end portion configured to penetrate tissue, said distal end portion being electrically and thermally conductive for establishing electric and thermal communication with the tissue;

a heat sink operatively connected to the ablation needle, the heat sink being connected to the ablation needle to draw energy away from at least the distal end portion thereof, the heat sink including a proximal end extending into the chamber of the hub and a distal end extending substantially the length of the ablation needle, wherein the heat sink is fabricated from an anisotropic material;

a first conduit fluidly connected to the hub for delivering fluid into the chamber thereof from the source of fluid; and a second conduit fluidly connected to the hub for draining fluid from the chamber thereof, wherein the hub is configured to direct the cooling fluid from the first conduit over the proximal end of the heat sink and out the second conduit to withdraw energy from the proximal end of the heat sink.

16. The ablation electrode assembly according to claim 15, wherein the heat sink is fabricated from a graphite fiber.

17. The ablation electrode assembly according to claim 16, wherein the ablation needle defines a cavity therein.

18. The ablation electrode assembly according to claim 17, wherein the heat sink is disposed within the cavity of the ablation needle.

19. The ablation electrode assembly according to claim 18, wherein the cavity of the ablation needle extends to the distal end portion thereof, and wherein a distal end of the heat sink is in conductive engagement with a distal end surface of the cavity of the ablation needle.

20. The ablation electrode assembly according to claim 19, further comprising an insulative coating surrounding at least a portion of a length of the ablation needle.

21. The ablation electrode assembly according to claim 20, wherein the distal end portion of the ablation needle is exposed.

22. The ablation electrode assembly according to claim 16, wherein the heat sink encases at least a portion of a length of the ablation needle.

23. The ablation electrode assembly according to claim 22, wherein the distal end portion of the ablation needle is exposed.

24. The ablation electrode assembly according to claim 16, further comprising an insulative coating surrounding at least a portion of a length of the heat sink encasing the ablation needle.

25. The ablation electrode assembly according to claim 24, further comprising a thermal-sensing circuit electrically connected to the ablation needle for measuring a temperature of the ablation needle.

26. The ablation electrode assembly according to claim 25, wherein the ablation needle is solid.

27. The ablation electrode assembly according to claim 26, further comprising a plurality of ablation needles.

* * * * *